(12) United States Patent
Qiu

(10) Patent No.: US 10,136,677 B2
(45) Date of Patent: Nov. 27, 2018

(54) RETRACTABLE MOUTHPIECE AND ELECTRONIC CIGARETTE HAVING THE SAME

(71) Applicant: Joyetech Europe Holding GmbH, Zug (CH)

(72) Inventor: Weihua Qiu, Jiangsu (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 0 days.

(21) Appl. No.: 15/665,757

(22) Filed: Aug. 1, 2017

(65) Prior Publication Data
US 2018/0027885 A1 Feb. 1, 2018

(30) Foreign Application Priority Data
Aug. 1, 2016 (CN) ...................... 2016 2 0820512 U

(51) Int. Cl.
| | | |
|---|---|---|
| *A24F 47/00* | (2006.01) | |
| *A61M 15/06* | (2006.01) | |
| *H05B 1/02* | (2006.01) | |
| *A24F 7/00* | (2006.01) | |

(52) U.S. Cl.
CPC ........... *A24F 47/008* (2013.01); *A61M 15/06* (2013.01); *H05B 1/02* (2013.01); *A24F 7/00* (2013.01); *A24F 47/00* (2013.01); *A61M 2205/75* (2013.01)

(58) Field of Classification Search
CPC ..... A24F 47/002; A24F 47/006; A24F 47/008
See application file for complete search history.

(56) References Cited

U.S. PATENT DOCUMENTS

| | | | | |
|---|---|---|---|---|
| 9,883,699 | B2 * | 2/2018 | Zhu ...................... | A24F 47/008 |
| 9,999,245 | B1 * | 6/2018 | Zhu ...................... | A24F 47/008 |
| 2012/0012617 | A1 * | 1/2012 | Gill ........................... | A45F 3/20 |
| | | | | 222/212 |
| 2013/0247910 | A1 * | 9/2013 | Postma ................ | A61M 11/041 |
| | | | | 128/203.26 |
| 2013/0312742 | A1 * | 11/2013 | Monsees ............... | A61M 15/06 |
| | | | | 128/202.21 |
| 2016/0022933 | A1 * | 1/2016 | Ciancone .......... | A61M 15/0086 |
| | | | | 128/200.23 |
| 2016/0050975 | A1 * | 2/2016 | Worm ................... | A24F 47/008 |
| | | | | 131/328 |
| 2017/0099877 | A1 * | 4/2017 | Worm .................. | A61M 11/042 |
| 2017/0215479 | A1 * | 8/2017 | Kies .......................... | A24F 3/00 |
| 2017/0367406 | A1 * | 12/2017 | Schuler ................ | A24F 47/008 |
| 2018/0027885 | A1 * | 2/2018 | Qiu .......................... | H05B 1/02 |
| 2018/0116294 | A1 * | 5/2018 | Saydar .................. | A61M 15/00 |
| 2018/0177230 | A1 * | 6/2018 | Hawes .................. | A24F 47/008 |

* cited by examiner

*Primary Examiner* — James Harvey
(74) *Attorney, Agent, or Firm* — Novick, Kim & Lee, PLLC; Allen Xue

(57) ABSTRACT

A retractable mouthpiece includes an upper cover of a hollow structure with an receiving cavity, a lower cover that fits with the upper cover, a fastener arranged between the upper cover and the lower cover and housed inside the receiving cavity, a smoking pipe housed inside the receiving cavity, and an elastic component arranged between the smoking pipe and the lower cover. The fastener is sleeved on the smoking pipe, and the smoking pipe is extended out of the upper cover or retracted within the upper cover when the smoking pipe is pressed or rotated. The retractable mouthpiece is both healthy and convenient. An electronic cigarette with the retractable mouthpiece is disclosed.

20 Claims, 3 Drawing Sheets

RETRACTABLE MOUTHPIECE AND ELECTRONIC CIGARETTE HAVING THE SAME

FIELD

The present disclosure relates to the technical field of electronic cigarette, and more particularly, to a retractable mouthpiece and an electronic cigarette having the same.

BACKGROUND

For an existing electronic cigarette, its mouthpiece is generally removably mounted to a main body of the electronic cigarette by a mechanically pluggable connection. Since the mouthpiece has a certain length, the overall length of the electronic cigarette with the mouthpiece is increased and thus not convenient for the user to carry. And if the user carries the electronic cigarette with the mouthpiece removed, it may likely result in the loss of the mouthpiece. In addition, in the existing electronic cigarette, the mouthpiece is generally exposed and vulnerable to external pollution, thereby affecting the user.

SUMMARY

In view of the above deficiencies in the prior art, an objective of the present disclosure is to provide a retractable mouthpiece, which is both healthy and convenient.

Furthermore, another objective of the present disclosure is to provide an electronic cigarette having the retractable mouthpiece.

In order to achieve the above objectives, the present disclosure proposes the following technical solutions. According to an aspect of the present disclosure, a retractable mouthpiece is provided, including an upper cover of a hollow structure with an receiving cavity, a lower cover that fits with the upper cover, a fastener arranged between the upper cover and the lower cover and housed inside the receiving cavity, a smoking pipe housed inside the receiving cavity, and an elastic component arranged between the smoking pipe and the lower cover, wherein the fastener is sleeved on the smoking pipe, and the smoking pipe is extended out of the upper cover or retracted within the upper cover when the smoking pipe is pressed and/or rotated.

Further, the fastener includes an upper surface, a lower surface arranged opposite to the upper surface, a plurality of upper clamping components extending upward from the upper surface, and a plurality of lower clamping components extending downward from the lower surface.

Further, each upper clamping component includes an upper protruding part protruding upward from the upper surface and an upper clamping part protruding outward from the upper protruding part, each lower clamping component includes a lower protruding part protruding downward from the lower surface and a lower clamping part protruding outward from the lower protruding part, both sides of each upper protruding part and each upper clamping part are inwardly slanted along a direction of an outer surface to an inner surface of the fastener, and both sides of each lower protruding part and each lower clamping part are inwardly slanted along the direction of the outer surface to the inner face of the fastener.

Further, the upper cover includes an upper cover body, an inner wall of an lower part of the upper cover body is provided with a protruding part protruding inward, the protruding part is provided with a protruding inner wall, the upper cover further includes a boss protruding inward from the protruding inner wall, and the upper clamping components are adapted to be engaged with the boss or abut against the boss when the smoking pipe is retracted.

Further, the lower clamping components are adapted to be engaged with the boss when the smoking pipe is extended.

Further, the upper clamping components are adapted to be separated from the boss by the elastic component when the smoking pipe is pressed, and the smoking pipe is extended out of the upper cover.

Further, the upper clamping components are adapted to be abut against the boss when the smoking pipe is pressed, and the smoking pipe is retracted into the receiving cavity.

Further, the upper clamping components are adapted to be separated from the boss when the smoking pipe is rotated, and the smoking pipe is extended out of the upper cover.

Further, the upper clamping components are adapted to be engaged with the boss or abut against the boss when the smoking pipe is pressed and then rotated, and the smoking pipe is retracted into the receiving cavity.

Further, the upper clamping components and the lower clamping components are arranged in a staggered manner or in an alignment manner in an axial direction.

Further, the upper cover and/or the smoking pipe are provided with an indicator indicating a position to be rotated and/or pressed.

According to another aspect of the present disclosure, an electronic cigarette is provided, including any one of the above retractable mouthpieces.

Compared with the prior art, the retractable mouthpiece and the electronic cigarette having the same according to the present disclosure have at least the following advantages: the upper clamping components or the lower clamping components of the fastener in the retractable mouthpiece can be cooperated with the boss of the upper cover when the smoking pipe is pressed and/or rotated, and the smoking pipe can be extended out of or retracted into the receiving cavity by the elastic force of the elastic component, so that the smoking pipe can be prevented from being frequently exposed and subjected to external pollution, and it is thus both healthy and convenient.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF PREFERRED EMBODIMENTS

In the following description of embodiments, reference is made to the accompanying drawings which form a part hereof, and in which it is shown by way of illustration specific embodiments of the present invention that can be practiced. It is to be understood that other embodiments can be used and structural changes can be made without departing from the scope of the disclosed embodiments.

Figure 1:
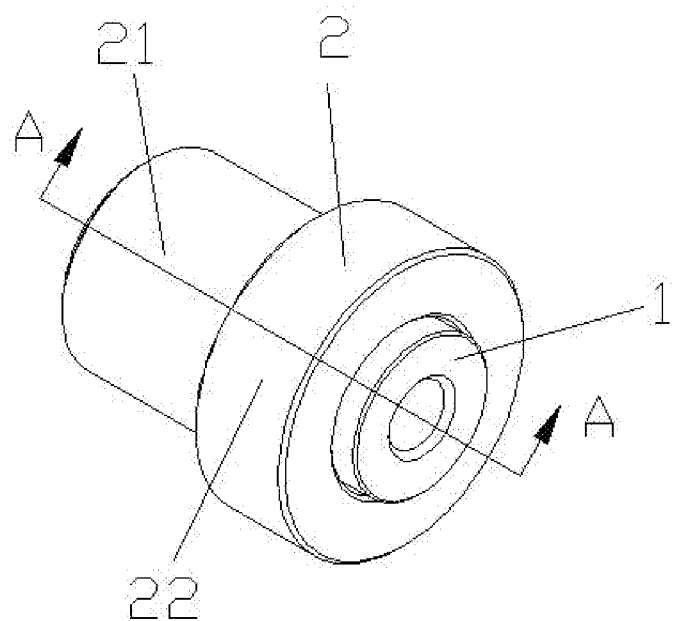
FIG. 1 is a schematic diagram illustrating a retractable mouthpiece according to one embodiment of the present disclosure when its smoking pipe is retracted.
Figure 2:
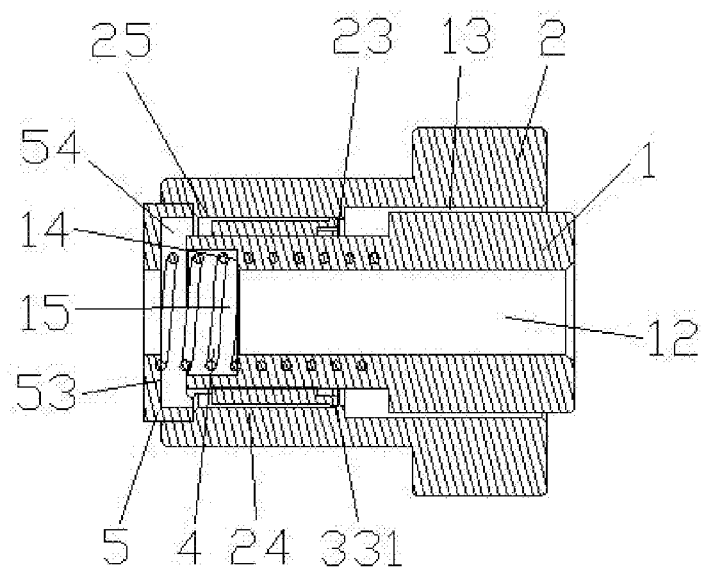
FIG. 2 is a cross-sectional view of the retractable mouthpiece in FIG. 1 along the A-A direction.
Figure 3:
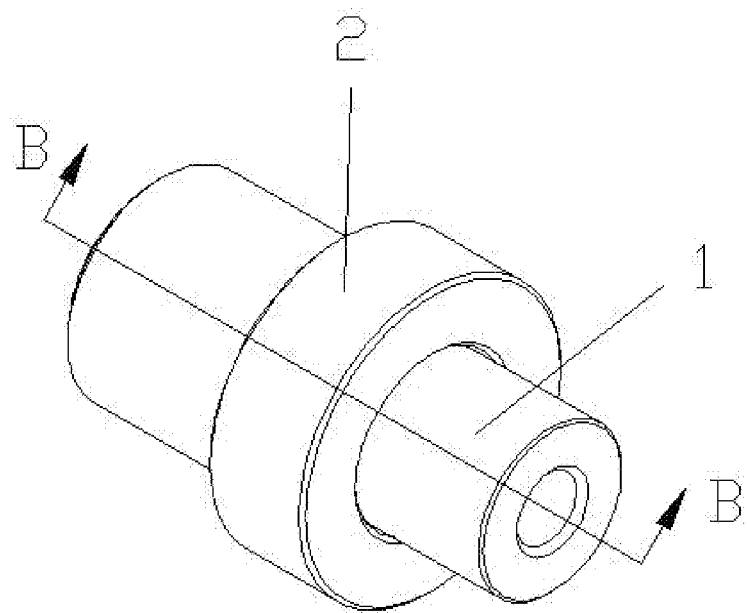
FIG. 3 is a schematic diagram illustrating a retractable mouthpiece according to one embodiment of the present disclosure when its smoking pipe is extended.
Figure 4:
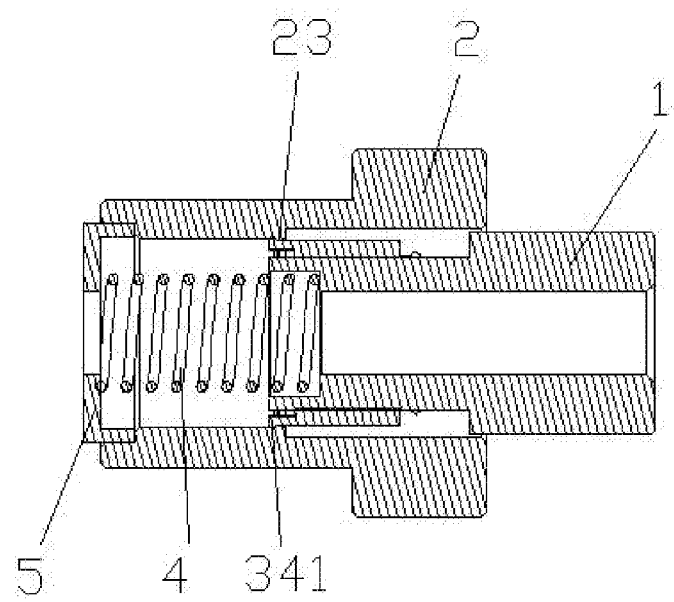
FIG. 4 is a cross-sectional view of the retractable mouthpiece in FIG. 3 along the B-B direction.
Figure 5:
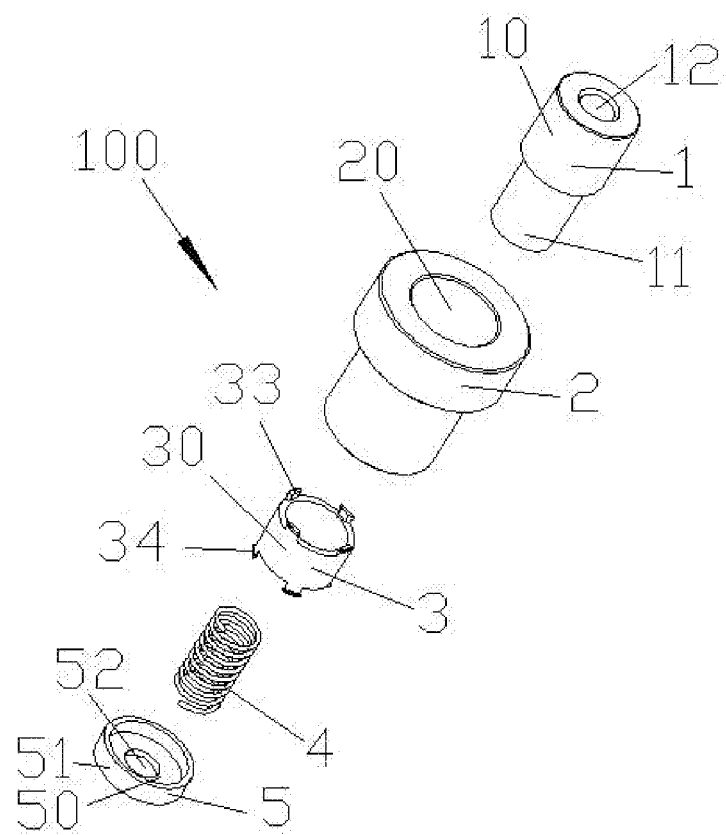
FIG. 5 is an exploded view of the retractable mouthpiece according to one embodiment of the present disclosure.
Figure 6:
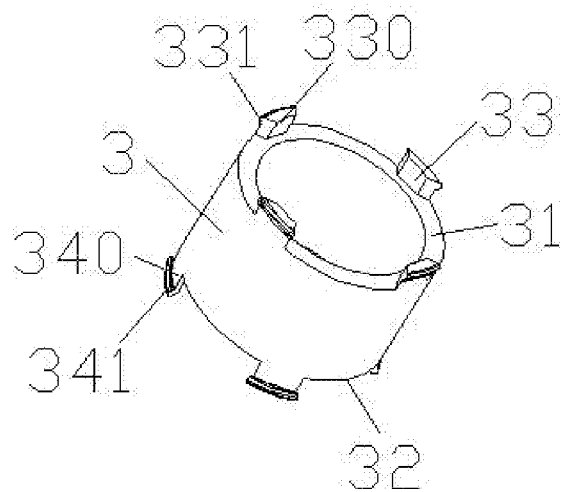
FIG. 6 is a schematic diagram illustrating a fastener of the retractable mouthpiece according to one embodiment of the present disclosure.

As shown in FIGS. 1 to 6, in an embodiment of the present disclosure, the retractable mouthpiece 100 includes a smoking pipe 1, an upper cover 2, a fastener 3, an elastic component 4 and a lower cover 5. The smoking pipe 1 and the fastener 3 are housed inside the upper cover 2. The fastener 3 is affixed to the smoking pipe 1 by interference fit. The fastener 3 is moveable within the upper cover 2. The upper cover 2 is fastened with the lower cover 5. The elastic component 4 is located between the smoking pipe 1 and the lower cover 5. The top end of the elastic component 4 abuts against the smoking pipe 1, and the opposite bottom end of the elastic component 4 abuts against the lower cover 5. The elastic component 4 is retractable within the upper cover 2, thereby driving the smoking pipe 1 to be extended out of the upper cover 2 or retracted within the upper cover 2.

The smoking pipe 1 has a step-shaped structure, including a main body portion 10, a fitting portion 11 extended downward from the main body portion 10, and a smoking channel 12 extending through the main body portion 10 and the fitting portion 11. The cross-sectional area in the radial direction of the main body portion 10 is larger than that of the fitting portion 11. The fitting portion 11 is receivable by the fastener 3. The bottom of the smoking pipe 1 defines a receiving hole 15, and the top of the receiving hole 15 is provided with a top wall 14.

The upper cover 2 has a hollow structure, including an upper cover body 21, a step portion 22 extending upward from the upper cover body 21, and a receiving cavity 20 passing through the upper cover body 21 and the step portion 22. The cross-sectional area in the radial direction of the step portion 22 is larger than that of the upper cover body 21, thus the step portion 22 and the upper cover body 21 are combined to form a step-shaped structure. The upper cover body 21 has a protruding part 24 inwardly extending from the inner surface of the lower end thereof. The protruding part 24 has a protruding inner wall 25. The upper cover 2 further includes a boss 23 protruding inward from the protruding inner wall 25.

The fastener 3 is sleeved on the fitting portion 11 of the smoking pipe 1, and tightly fits over the fitting portion 11 so as to affix the fastener 3 onto the smoking pipe 1 and to restrict the movement of the smoking pipe 1 in the axial direction. The fastener 3 includes a fastener body 30 of an annular shape. The fastener body 30 includes an upper surface 31 and a lower surface 32 arranged opposite to the upper surface 31, a plurality of upper clamping components 33 extending upward from the upper surface 31 and a plurality of lower clamping components 34 extending downward from the lower surface 32. Each upper clamping component 33 includes an upper protruding part 330 protruding upward from the upper surface 31 and an upper clamping part 331 protruding outward from the upper protruding part 330. Each lower clamping component 34 includes a lower protruding part 340 protruding downward from the lower surface 32 and a lower clamping part 341 protruding outward from the lower protruding part 340. The fastener body 30 has an outer surface and an inner face, both sides of the upper protruding part 330 and the upper clamping part 331 are inwardly slanted along a direction of the outer surface to the inner face of the fastener body 30, and both sides of the lower protruding part 340 and the lower clamping part 341 are inwardly slanted along the direction of the outer surface to the inner face of the fastener body 30. The upper clamping components 33 and the lower clamping components 34 are arranged in a staggered manner in the axial direction, that is, the upper clamping components 33 and the lower clamping components 34 are staggered along the top to bottom direction of the fastener 3. Alternatively, the upper clamping components 33 and the lower clamping components 34 can be aligned in the axial direction. That is, the upper clamping components 33 and the lower clamping components 34 are symmetrically arranged along the radial direction of the fastener 3. In this embodiment, the number of the upper clamping components 33 is equal to the number of the lower clamping components 34, which may be one, two, three, and so forth. And the upper clamping components 33 and the lower clamping components 34 may be provided in pairs, that is, the upper clamping component 33 and the lower clamping component 34 can be provided in various manners so long as the function of the clamping can be achieved. The upper clamping components 33 are spaced apart from each other to define a gap, and arranged parallel to the axial direction of the smoking pipe 1. The lower clamping components 34 are also spaced apart from each other to define a gap, and arranged parallel to the axial direction of the smoking pipe 1. The upper clamping components 33 can be evenly spaced. The lower clamping components 34 can be also evenly spaced. The gap between adjacent upper clamping components 33 is equal to the gap between adjacent lower clamping components 34. Alternatively, the number of the upper clamping components 33 can be different from the number of the lower clamping components 34. Alternatively, the gap between adjacent upper clamping components 33 can be different from the gap between adjacent lower clamping components 34.

The lower cover 5 is of a concave shape, including a bottom 50, an extending wall 51 extending upward from the circumference of the bottom 50, and a receiving space 54 enclosed by the bottom 50 and the extending wall 51. The center of the bottom 50 defines a through-hole 52 passing through the bottom 50. The bottom 50 further includes a bottom wall 53 facing the elastic component 4. The top end of the elastic component 4 abuts against the top wall 14 and the bottom end abuts against the bottom wall 53. The elastic component 4 may be a spring or an elastomer with elasticity. The elastic component 4 is housed inside the receiving space 54 and the receiving hole 15 when the elastic component 4 is compressed, and the elastic component 4 is housed inside the receiving space 54, the receiving hole 15 and the receiving cavity 20 when the elastic component 4 is extended. There is a gap 13 between the outer surface of the main body portion 10 of the smoking pipe 1 and the inner surface of the upper part of the receiving cavity 20, and there is a gap between the outer surface of the fastener body 30 of the fastener 3 and the protruding inner wall 25, so as to facilitating the extending and retracting of the smoking pipe within the receiving cavity 20.

The smoking pipe 1 can be extended out of the upper cover 2 and retracted within thereof. In one embodiment, when the smoking pipe 1 is in the retracted state, the fastener 3 is affixed to the fitting portion 11 of the smoking pipe 1, and the smoking pipe 1 is housed inside the receiving cavity 20. At this time, the elastic component 4 is in a compressed state, and the upper clamping parts 331 of the upper clamping components 33 abut against the boss 23, so that the smoking pipe 1 cannot be pushed out by the elastic force of the elastic component 4. When the smoking pipe 1 is required to be extended, the smoking pipe 1 is pressed so that the upper clamping parts 331 are separated from the boss 23, and the smoking pipe 1 is pushed out with the elastic force of the elastic component 4. At this time, the lower clamping parts 341 are engaged with the boss 23 so that the smoking pipe 1 is restricted from being further extended outward. Then, when the smoking pipe 1 that has been pushed out is pressed inward, the upper clamping parts 331 may deform elastically and move over the boss 23, and then abuts against the boss 23, thereby the smoking pipe 1 comes back to the retracted state. The upper clamping parts 331 can be made of elastic material. The upper clamping components 33 and the lower clamping components 34 are arranged in an alignment manner in the axial direction. That is, the upper clamping components 33 and the lower clamping components 34 are symmetrically arranged along the radial direction of the fastener 3. Therefore, the boss 23 can abuts against the upper clamping components 33 or engage with the lower clamping components 34, when the fastener 3 and the smoking pipe 1 are moved relatively along the axis of smoking pipe 1 under the pressing action. It will be appreciated that the boss 23 can be provided on the protruding inner wall 25 in a circumferential direction. So that the boss 23 can cooperate with the upper clamping components 33 or the lower clamping components 34 under the pressing action to restrict the movement of the smoking pipe 1, regardless of whether the upper clamping components 33 and the lower clamping components 34 are symmetrically arranged along the radial direction of the fastener 3 or staggered along an up to down direction of the fastener 3.

In another embodiment, the extending and retracting of the retractable mouthpiece 100 may also be achieved by rotating and/or pressing the smoking pipe 1. For example, if the smoking pipe 1 is rotated so that the upper clamping parts 331 are separated from the boss 23, the smoking pipe 1 is pushed out for a certain distance with the elastic force of the elastic component 4, while the boss 23 comes to engage with the lower clamping parts 341, thus preventing the smoking pipe 1 from being further extended outward. At this time, the retractable mouthpiece 100 is in the extended state. When the smoking pipe 1 that has been pushed out is pressed inwardly in a certain distance and then rotated in a certain angle, the upper clamping parts 331 cooperate with the boss 23, and thereby the smoking pipe 1 comes back to the retracted state. The upper clamping parts 331 cooperating with the boss 23 in such a manner that the upper clamping parts 331 engage with the boss 23, or the upper clamping parts 331 abut against the boss 23. The upper clamping components 33 and the lower clamping components 34 are provided in a staggered manner. It will be appreciated that the protruding inner wall 25 can be further provided with a guide groove (not shown), and the lower clamping parts 341 can move along the guide groove. The cooperation of the lower clamping parts 341 and the guide groove can guide the user operation of rotating and pressing the smoking pipe 1. That is, in the process which the smoking pipe 1 is extended out of the upper cover 2 or retracted within thereof, the movement path of the smoking pipe 1 coincides with the movement path of the lower clamping parts 341 along the guide groove.

In the above two embodiments, the upper cover 2 and/or the smoking pipe 1 are provided with an indicator indicating a position to be rotated or pressed.

The present disclosure further provides an electronic cigarette with the above-mentioned retractable mouthpiece 100.

For the retractable mouthpiece 100 and the electronic cigarette having the same, the upper clamping components 33 or the lower clamping components 34 of the fastener 3 in the retractable mouthpiece 100 can be cooperated with the boss 23 of the upper cover 2 when the smoking pipe 1 is pressed and/or rotated, and the smoking pipe 1 can be extended out of or retracted into the receiving cavity 20 by the elastic force of the elastic component, so that the smoking pipe 1 can be prevented from being frequently exposed and subjected to external pollution, and it is thus both healthy and convenient.

The above are preferred embodiments of the present disclosure described in detail, and should not be deemed as limitations to the scope of the present disclosure. It should be noted that variations and improvements will become apparent to those skilled in the art to which the present disclosure pertains without departing from its spirit and scope. Therefore, the scope of the present disclosure is defined by the appended claims.

What is claimed is:
1. A retractable mouthpiece, comprising:
an upper cover of a hollow structure with a receiving cavity;
a lower cover that fits with the upper cover;
a fastener arranged between the upper cover and the lower cover and housed inside the receiving cavity;
a smoking pipe housed inside the receiving cavity; and
an elastic component arranged between the smoking pipe and the lower cover,
wherein the fastener is sleeved on the smoking pipe, and the smoking pipe is extended out of the upper cover or retracted within the upper cover when the smoking pipe is pressed and/or rotated.

2. The retractable mouthpiece according to claim 1, wherein the fastener includes an upper surface, a lower surface arranged opposite to the upper surface, a plurality of upper clamping components extending upward from the upper surface, and a plurality of lower clamping components extending downward from the lower surface.

3. The retractable mouthpiece according to claim 2, wherein each upper clamping component includes an upper protruding part protruding upward from the upper surface and an upper clamping part protruding outward from the upper protruding part, each lower clamping component includes a lower protruding part protruding downward from the lower surface and a lower clamping part protruding outward from the lower protruding part, both sides of each upper protruding part and each upper clamping part are inwardly slanted along a direction of an outer surface to an inner surface of the fastener, and both sides of each lower protruding part and each lower clamping part are inwardly slanted along the direction of the outer surface to the inner face of the fastener.

4. The retractable mouthpiece according to claim 2, wherein the upper cover includes an upper cover body, an inner wall of a lower part of the upper cover body is provided with a protruding part protruding inward, the protruding part is provided with a protruding inner wall, the upper cover further includes a boss protruding inward from the protruding inner wall, and the upper clamping components are adapted to be engaged with the boss or abut against the boss when the smoking pipe is retracted.

5. The retractable mouthpiece according to claim 4, wherein the lower clamping components are adapted to be engaged with the boss when the smoking pipe is extended.

6. The retractable mouthpiece according to claim 4, wherein the upper clamping components are adapted to be separated from the boss by the elastic component when the smoking pipe is pressed, and the smoking pipe is extended out of the upper cover.

7. The retractable mouthpiece according to claim 6, wherein the upper clamping components are adapted to be abut against the boss when the smoking pipe is pressed, and the smoking pipe is retracted into the receiving cavity.

8. The retractable mouthpiece according to claim 4, wherein the upper clamping components are adapted to be separated from the boss when the smoking pipe is rotated, and the smoking pipe is extended out of the upper cover.

9. The retractable mouthpiece according to claim 8, wherein the upper clamping components are adapted to be engaged with the boss or abut against the boss when the smoking pipe is pressed and then rotated, and the smoking pipe is retracted into the receiving cavity.

10. The retractable mouthpiece according to claim 2, wherein the upper clamping components and the lower clamping components are arranged in a staggered manner or in an alignment manner in a axial direction.

11. The retractable mouthpiece according to claim 1, wherein the upper cover and/or the smoking pipe are provided with an indicator indicating a position to be rotated and/or pressed.

12. An electronic cigarette, comprising:
    a retractable mouthpiece comprising:
        an upper cover of a hollow structure with a receiving cavity;
        a lower cover that fits with the upper cover;
        a fastener arranged between the upper cover and the lower cover and housed inside the receiving cavity;
        a smoking pipe housed inside the receiving cavity; and
        an elastic component arranged between the smoking pipe and the lower cover,
        wherein the fastener is sleeved on the smoking pipe, and the smoking pipe is extended out of the upper cover or retracted within the upper cover when the smoking pipe is pressed and/or rotated.

13. The electronic cigarette according to claim 12, wherein the fastener includes an upper surface, a lower surface arranged opposite to the upper surface, a plurality of upper clamping components extending upward from the upper surface, and a plurality of lower clamping components extending downward from the lower surface.

14. The electronic cigarette according to claim 13, wherein each upper clamping component includes an upper protruding part protruding upward from the upper surface and an upper clamping part protruding outward from the upper protruding part, each lower clamping component includes a lower protruding part protruding downward from the lower surface and a lower clamping part protruding outward from the lower protruding part, both sides of each upper protruding part and each upper clamping part are inwardly slanted along a direction of an outer surface to an inner surface of the fastener, and both sides of each lower protruding part and each lower clamping part are inwardly slanted along the direction of the outer surface to the inner face of the fastener.

15. The electronic cigarette according to claim 13, wherein the upper cover includes an upper cover body, an inner wall of a lower part of the upper cover body is provided with a protruding part protruding inward, the protruding part is provided with a protruding inner wall, the upper cover further includes a boss protruding inward from the protruding inner wall, and the upper clamping components are adapted to be engaged with the boss or abut against the boss when the smoking pipe is retracted.

16. The electronic cigarette according to claim 15, wherein the lower clamping components are adapted to be engaged with the boss when the smoking pipe is extended.

17. The electronic cigarette according to claim 15, wherein the upper clamping components are adapted to be separated from the boss by the elastic component when the smoking pipe is pressed, and the smoking pipe is extended out of the upper cover.

18. The electronic cigarette according to claim 17, wherein the upper clamping components are adapted to be abut against the boss when the smoking pipe is pressed, and the smoking pipe is retracted into the receiving cavity.

19. The electronic cigarette according to claim 15, wherein the upper clamping components are adapted to be separated from the boss when the smoking pipe is rotated, and the smoking pipe is extended out of the upper cover.

20. The electronic cigarette according to claim 19, wherein the upper clamping components are adapted to be engaged with the boss or abut against the boss when the smoking pipe is pressed and then rotated, and the smoking pipe is retracted into the receiving cavity.

* * * * *